United States Patent [19]

Rudy et al.

[11] 3,932,610

[45] Jan. 13, 1976

[54] SHAMPOO COMPOSITION

[75] Inventors: Jerome Rudy, Livingston; Morton Pader, Teaneck; William Netzbandt, Dumont, all of N.J.

[73] Assignee: Lever Brothers Company, New York, N.Y.

[22] Filed: Mar. 21, 1973

[21] Appl. No.: 343,593

Related U.S. Application Data

[63] Continuation-in-part of Ser. No. 205,314, Dec. 6, 1971, abandoned.

[52] U.S. Cl. ................................................ 424/70
[51] Int. Cl.² ........................................... A61K 7/06
[58] Field of Search ....................................... 424/70

[56] References Cited
UNITED STATES PATENTS

| | | | |
|---|---|---|---|
| 2,756,178 | 7/1956 | Verblen | 424/70 |
| 3,533,955 | 10/1970 | Pader et al. | 424/70 |
| 3,634,264 | 1/1972 | Pence | 424/70 |
| 3,697,644 | 10/1972 | Laiderman | 424/70 |

*Primary Examiner*—Sam Rosen
*Attorney, Agent, or Firm*—Arnold Grant, Esq.

[57] ABSTRACT

The present invention relates to a shampoo composition having dissolved therein a hair grooming agent, which agent becomes insoluble upon dilution with water during shampooing, depositing on the hair to impart desirable properties to the hair, such as body, set, sheen and ease of combing. More particularly the present invention discloses a shampoo composition comprising a surfactant system, a solvent system, a hair grooming agent, soluble in the solvent and/or solvent surfactant/systems and insoluble in water, and, in preferred embodiments, a hair lubricant which may be dissolved or dispersed in the surfactant-solvent system or form part of a distinct phase in a multi-phase composition.

18 Claims, No Drawings

SHAMPOO COMPOSITION

This application is a continuation-in-part of application Ser. No. 205,314, filed Dec. 6, 1971, now abandoned.

BACKGROUND OF THE INVENTION

1. Field of the Invention

Foaming shampoos having dissolved or dispersed therein water-insoluble hair grooming agents.

2. Description of the Prior Art

Addition of hair conditioning agents such as polyglycols, fatty acid esters of glycols, waxes, protein and lanolin derivatives to single phase shampoo compositions to improve manageability and counteract the loss of natural oils caused by synthetic detergents are well known. These products are, however, only marginally satisfactory because they do not retain sufficient amounts of the agent on the hair after the shampooing rinse cycle to provide palpable results.

Products for this purpose are also available for application to the hair subsequent to shampooing, such as hair rinses, sets and sprays. These products often contain polymeric substances which form a film on the hair upon drying, thereby holding the hair in a desired preformed configuration, i.e., impart body and wave retention. To date, it has not been possible to satisfactorily incorporate these substances into a commercially acceptable water base shampoo formulation. For the most part, this is again because the substances, if soluble enough to be included in a homogenous shampoo composition are not attracted to the hair fiber in sufficient degree to prevent removal during the rinse cycle. In the instances (U.S. Pat. Nos. 2,756,178, 3,313,734 and 3,400,198) where lanolin and polymeric materials, e.g., polyethyleneimine, quaternized vinyl imidiazole and quaternized diethylaminoethyl methacrylate, etc., were found were incorporated into particular shampoo systems, the hair grooming agent was either water soluble and tended to both dull the hair and adversely affect the feel of the hair or deposition on the hair was a random event depending on large quantities of the hair grooming agent in the shampoo composition and inefficient rinsing by the user to obtain any substantive effect.

SUMMARY OF THE INVENTION

The present invention has found a method of incorporating water insoluble resinous and waxy materials into an aqueous base shampoo composition which will be retained on the hair after rinsing, so that, in addition to normal cleansing action, desirable grooming benefits can be imparted to the hair such as body, set holding, sheen and ease of combing. In its most basic form, the shampoo composition of the present invention comprises: (1) a surfactant system, which may be soap and/or a synthetic detergent; (2) a solvent system; and, (3) a water-insoluble hair grooming agent which is substantially soluble in the solvent and/or a combination of the solvent/surfactant; the hair grooming agent being made soluble in the water base shampoo composition by the solvent and/or solvent/surfactant and becoming insoluble in the shampoo composition and depositing onto the hair by addition of water during the shampooing and shampooing rinse cycle according to a dilution-deposition type mechanism. In the preferred form, the shampoo composition further comprises a hair lubricant which may be soluble, dispersible or insoluble in the solvent and/or solvent/surfactant to provide ease of combing and anti-stat properties to the hair after use.

The solvent system, which may be capable of dissolving the surfactant and, either alone or in conjunction with the surfactant is capable of substantially dissolving the hair grooming agent, should contain at least about 10 percent, based on the weight of the solvent system, of at least one water miscible substantially polar organic solvent. Additionally, the solvent system may also contain up to about 40 percent of the weight of the polar organic solvent, of a non-polar solvent to enhance solubility of the grooming agent in the system.

The hair grooming agent, most preferably, imparts body or set holdability to the hair, although agents which condition or instill sheen are similarly preferred. The grooming agent may be in the form of a resin, a wax, a liquid or combinations thereof; the requirements of the agent being that they are made substantially soluble in an aqueous base shampoo composition by the solvent and/or solvent/surfactant system; are substantially insoluble in the amounts of water normally used in the shampooing and rinse operations; are essentially non-deleterious to the detergency of the surfactant system; and they impart a desirable beneficial quality to the hair when used in this manner. It is believed that during the dilution with water which occurs in the shampooing and rinse cycles of the shampoo operation, the hair grooming agent forms a discrete particle dispersion, resulting in a partitioning of the grooming agents from the diluted shampoo composition to the hair shaft. This dispersion-deposition mechanism permits the wet insoluble grooming agent to become affixed to the hair without subsequent removal during continuation of the rinse cycle.

The hair lubricant, for the preferred form of the present invention may be soluble, dispersable or insoluble in the composition, i.e., form a separate phase of a multi-phase system. When soluble or dispersable in the composition, the lubricant should be present from about 1 to about 15 weight percent, based on the weight of the total composition; when insoluble, forming a separate phase, it is preferred to increase the upper limit to about 25 weight percent with a desired range being from about 5 to about 20 weight percent.

DETAILED DESCRIPTION OF THE INVENTION

The shampoo compositions of the present invention are intended to provide detergency while simultaneously imparting one or more desirable grooming effects to the hair such as body, set holding, sheen, softness, conditioning and ease of combing. In its most basic form the invention herein comprises a surfactant system, a solvent system, and a dissolved or dispersed water-insoluble hair grooming agent. In its preferred form the composition further contains a combing agent to impart conditioning, anti-stat, ease of combing and the like.

The surfactant system comprises one or more water-soluble surface-active agents, i.e., an anionic, nonionic, or amphoteric surfactant, or a mixture thereof, which produces acceptable foam or whose foam is supplemented by a suds improver. Preferred anionic detergents are sulfonated and sulfated anionic detergents and in particular the sodium, magnesium, ammonium, mono- di- and triethanolamine salts of sulfated fatty alcohols as well as these salts of the sulfonated alkylaryl compounds, all of which have a total of from 12 to 21 carbon atoms. Typical anionic detergents include sodium lauryl sulfate, sodium oleyl succinate, ammonium lauryl sulfosuccinate, sodium lauryl ether sulfate, ammonium lauryl sulfate, monoethanaolamine lauryl sulfate, triethanolamine lauryl sulfate, sodium dodecylbenzene sulfonate, triethanolamine dodecylbenzene sulfonate and sodium N-lauroyl sarcosinate. Other anionic detergents include soaps such as triethanolamine laurate-myristate and triethanolamine oleate.

Nonionic detergents include fatty acid alkanolamides and the alkylene oxide (ethylene oxide and propylene oxide) condensates of a hydrophobic base such as a long chain fatty alcohol or an alkylphenol. Typical of the fatty acid alkanolamides are those having a total of from 10 to 21 carbon atoms, such as lauric diethanolamide, coconut oil monoethanolamide and lauric isopropanolamide. The alkylene oxide condensates of long chain fatty alcohols include $C_{10}$ to $C_{21}$ fatty alcohols condensed with 3 to 20 moles of ethylene oxide, such as the ethylene oxide condensates of lauryl alcohol, myristyl alcohol and palmityl alcohol. The alkylene oxide condensates of alkylphenols include the alkylphenols having a $C_8$ to $C_{15}$ alkyl group condensed with 3 to 20 moles of ethylene oxide, such as the octylphenol-8 mole ethylene oxide condensate, the nonyl phenol-10 mole ethylene oxide condensate and the dodecyl phenol-10 mole ethylene oxide condensate.

Amphoteric or ampholytic detergents include N-lauryl-N'-carboxymethyl-N'-(2-hydroxyethyl) ethylenediamine, coco-beta-alanine, and the Miranol compounds described in U.S. Pat. Nos. 2,528,378 and 2,781,354.

Other examples, well known to the art, may be found in the literature such as "Surface Active Agents" by Schwartz and Perry and "Surface Active Agents and Detergents" by Schwartz, Perry and Berch, both Interscience Publishers, New York, New York, the disclosures of which are incorporated herein.

The most preferred detergents are the anionics such as the lauryl sulfates, particularly monoethanolamine, triethanolamine and ammonium lauryl sulfates. Sodium lauryl sulfate and sodium lauryl ether sulfate are also very suitable for use in the compositions of the invention. Preferably the surfactant system is present in an amount of from about 5 to about 60 percent, more preferably from about 7 to about 40 percent and most preferably from about 10 to about 30 percent by weight of the composition. Compositions containing lower amounts of surfactant than this do not clean the hair well and also give low foam volumes, while those containing greater amounts effect too great a dispersibility of the resin for deposition on the hair and introduce problems of eye irritancy.

Optionally, the detergent system may also contain, from about 0.2 to about 15 weight percent, based on the weight of the total composition, of one or more lather boosters and/or stabilizers, to increase sudsing power and foam stability. Examples of these would include coco amide, lauric diethanolamide, lauric isopropanolamide, coconut monoethanol amide, betaines, sulfobetaines, coco, dimethyl amide oxide, coco bis 2-hydroxyethyl amide oxide, the most preferred of these lather adjuvants are lauric diethanolamide, lauric isopropanol amide, coco amide, and coco bis 2-hydroxyethyl amine oxide.

The solvent system, which may dissolve the surfactant and either alone or in conjunction with the surfactant, will be capable of substantially dissolving the grooming agent so that the grooming agent-solvent will form a single phase system in the aqueous base shampoo, should contain at least about 10 weight percent preferably, from about 14 to about 70 percent, based on the weight of the solvent system, of at least one water miscible, substantially polar organic solvent. The solvent system should be present in the composition from about 10 to about 90 weight percent, based on the weight of the total composition, preferably 12–80 weight percent and most preferably 18–50 weight percent. Examples of polar solvents suitable either alone or in combination with other solvents for purposes of the present invention include monohydric alcohols having from 2 to 12 carbon atoms such as ethyl alcohol, n-propanol, isopropanol and higher fatty alcohols such as lauryl alcohol, dihydric alcohols such as dipropylene glycol, and polyethylene glycols (MW 400), triols such as glycerol and ethers such as monoethyl ether of ethylene glycol and monoethyl ether of diethylene glycols. The most preferred polar solvents are ethyl alcohol, n-propanol, and isopropanol.

The solvent system may, to enhance retention of the hair grooming agent in solution, additionally contain up to about 40 weight percent, based on the polar organic solvent, of a non-polar solvent. Examples of non-polar solvents suitable for purposes of the invention would include hydrocarbons, i.e., mineral spirits, chlorinated hydrocarbons such as methylene chloride and fluorinated hydrocarbons such as trichlorotrifluorethane.

The term "hair grooming agent" as used herein is intended to describe a material which upon use according to the manner of the present invention imparts a desirable benefit or quality to the hair and is either resinous, waxy or a liquid, or a mixture thereof, is substantially soluble, as herein defined, in the solvent and/or solvent/surfactant systems of the present invention and is substantially insoluble, as herein defined, in water. Particular benefits sought to be imparted to the hair would include body (i.e., a feeling of thickness, substance or weight), set holding, wave retention and conditioning, etc.; selection of the grooming agent will depend upon the particular benefit or combination of benefits sought to be imparted to the hair.

The term "substantially soluble" as used herein to describe a required property of the hair grooming agent will be completely dissolved in 100 grams of ethyl alcohol. The term "substantially insoluble" as used herein to define a property of the hair grooming agent relative to water means that in the absence of the solvent and/or solvent/surfactant less than 10 grams of the hair grooming agent will be dissolved in 100 grams of water.

Thus, the hair grooming agent must impart a desirable benefit or quality to the hair when used according to the present invention, must be substantially soluble in the solvent and/or solvent/surfactant systems, must be rendered substantially soluble in a water base shampoo by the solvent and/or solvent/surfactant systems, must be substantially insoluble, precipitating from solution upon addition of the relatively large amounts of water normally used in the shampoo and rinse operations, and, be essentially non-deleterious to the detersive action of the surfactant system. Hereinafter, the term solvent/surfactant will be used to denote the group solvent and solvent/surfactant. That is, the hair grooming agent is substantially soluble in the solvent-surfactant implies that the hair grooming agent is substantially soluble in the solvents per se, and/or substantially soluble in a combination of the solvents and surfactants. The grooming agent or combination of agents should be present in amount from about 1.0 to about 60 weight percent, based on the weight of the total composition, preferably from about 4 to about 40 weight percent and most preferably from about 4 to about 20 weight percent. At levels of less than about 1.0 weight percent an insufficient quantity of grooming agent is retained on the hair after rinse resulting in loss of the desired benefit; at levels of greater than about 60 weight percent the grooming agent tends to interfere with the detersive action of the surfactant system and to give rise to objectionable properties such as tackiness, poor combing and flaking, etc.

Resinous materials, in general, tend to impart bodying or set holding to the hair. Suitable resins for purposes of the present invention would include wood rosins and the $C_1$ to $C_6$ esters thereof, the wood rosins and esters preferably having a softening point of between about 96°C to about 125°C and a Gardner-Holt viscosity of between about 20 and 40. Preferred embodiments of these rosins and their $C_1$ to $C_6$ esters are polymerized and dimerized rosins (softening point 98°–106°C acid number 140 minimum), hydrogenated rosin (softening point 69°–80°C, acid number 158 minimum) and hydrogenated methyl ester of rosin (boiling point 350°–380°C preferably 360°–364°C, acid number 7 minimum). Other suitable resins are sucrose acetate isobutyrate, polyvinyl ethyl ether resin having a molecular weight of from about 10,000–750,000, alkyd resins having a preferred molecular weight of from about 10,000–50,000, polyketone resins having a preferred average molecular weight of from about 500–1,000, most preferably 600–800, vinyl acetate resins having an average molecular weight of from about 8,000–15,000, acrylic resins having an average molecular weight of from about 10,000–150,000 and the like and mixtures thereof.

Waxy materials tend to impart bodying and conditioning effects to the hair. Suitable waxy materials would include, but are not limited to, cocoamide (preferably having a melting point of 80°–90°C), ethoxylated lanolin containing about 5 to about 25 moles of ethylene oxide, stearyl amide (preferably having a melting point of 95°–110°C), ethoxylated higher fatty alcohols, preferably $C_{14}$–$C_{30}$ having 2 to 4 moles of ethylene oxide, and the like. Liquid grooming agents such as lanolin alcohols (preferably having a viscosity of 10–30 cps. at 20°C), cetylated castor oil (preferably having a saponification value of about 144–150), mineral oil fractions having a Saybolt viscosity of about 50 to about 360 sec., and the like tend to impart conditioning and ease of combing effects to the hair.

Preferred hair grooming agents are the above defined wood rosins, sucrose acetate isobutyrate and polyketone used alone or in combinations such as wood rosins — polyketone and sucrose acetate isobutyrate — polyketone at ratios from about 1:9 to about 9:1, most preferably 1:5 to 5:1. Combinations of hair grooming are desired because of the balance of desired benefits they provide.

In its preferred form the shampoo compositions according to the present invention further include from about 1 to about 25 weight percent, preferably from about 3 to about 12 weight percent based on the weight of the total composition; of a hair lubricant to provide conditioning and ease of combing after use. The hair lubricant may be soluble or dispersed in the surfactant-/solvent or, optionally, may be insoluble, forming a separate phase of a multi-phase system. Examples of soluble or dispersible lubricants which should be present from about 1 to 15 weight percent, would include, but are not limited to esters such as, isopropyl myristate and adipates, glycol polysiloxanes and relatively low levels of dissolved mineral oil, and mixtures thereof.

When the shampoo composition is constituted with an insoluble lubricant as a multi-phase system, of the type disclosed in U.S. Pat. No. 3,533,955, the disclosure of which is incorporated herein by reference, the composition may include from about 5 to about 25 percent, preferably about 5 to about 20 percent of one or more water-immiscible oily materials such as light mineral oils, preferably those having a Saybolt viscosities of 65–75 cps. at 100°F and a specific gravity of 0.835 at 60°F; fixed oils or animal and vegetable oils such as linseed oil, castor oil, olive oil, safflower oil, almond oil, peanut oil, coconut oil and fractions and sesame oil; and lanolin compounds such as the well known lanolin esters and lanolin alcohols. In this embodiment, it is necessary to further include in the shampoo composition from about 9 to about 28 weight percent, based on the weight of the total composition, of one or more emulsion destabilizers, examples of which would include the monohydric alcohols having from 1 to 7 carbon atoms, the monoalkyl ethers of an aliphatic dihydric alcohol having from 3 to 6 carbon atoms and the dialkyl ketones having a total of from 3 to 5 carbon atoms. These may simultaneously serve as the polar organic solvent component of the compositions of the present invention.

Optionally, the shampoo composition may further contain from about 0.1 to about 10 weight percent of a hydrophilic thickener to prevent localized deposition of the hair grooming agent, i.e., promote even distribution throughout the hair. Examples of suitable materials are hydroxypropyl cellulose, proteins, gelatin, methyl cellulose, pyrogenic silicas and polyoxyethylene.

The shampoo composition may, of course, also include, if desired such further adjuvants as perfumes or essential oils, dyes, silicones and the like to enhance and improve the commercial acceptability of the product. The remainder of the composition usually comprises water.

The following tables illustrate, without limiting, shampoo compositions prepared according to the present invention. The polyketone used in the examples has a molecular weight between about 600 to about 800 and a softening point in the range of from about 200 to about 220°F. The polyvinylacetate in the examples has an average molecular weight of about 12,800, a Ford Number viscosity of 4, measured at 25°C and a specific gravity of 1.18. The polyethyl ether resin used in the examples has a specific gravity of 0.973 at 20°C/20°C and a reduced viscosity at 20°C of 0.3+.01.

EXAMPLES

TABLE I

| | | Percent by weight Example No. | | | |
|---|---|---|---|---|---|
| | | 1 | 2 | 3 | 4 |
| triethanolamine lauryl sulfate | | 18.4 | 18.4 | 18.4 | 18.4 |
| hydrogenated rosin | | 10.0 | 5.0 | — | — |
| polymerized rosin | | — | — | 10.0 | 8.0 |
| ethyl alcohol | | 50.0 | 30.0 | — | — |
| isopropyl alcohol | | — | — | 40.0 | 40.0 |
| perfume | | 0.5 | 0.5 | 0.5 | 0.5 |
| water | | 21.1 | 46.1 | 31.1 | 33.1 |
| | total | 100.0 | 100.0 | 100.0 | 100.0 |

TABLE II

| | | Percent by weight Example No. | | | | | |
|---|---|---|---|---|---|---|---|
| | | 5 | 6 | 7 | 8 | 9 | 10 |
| triethanolamine lauryl sulfate | | 18.4 | 18.4 | 18.4 | 18.4 | 18.4 | 18.4 |
| polymerized rosin | | — | — | 10.0 | 10.0 | 10.0 | 10.0 |
| hydrogenated rosin | | 10.0 | 5.0 | — | — | — | — |
| ethyl alcohol | | 37.5 | 12.0 | 18.0 | 18.0 | 18.0 | 18.0 |
| mineral oil | | 7.0 | 5.0 | 10.0 | 10.0 | 10.0 | 4.0 |
| lauric isopropanolamide | | — | 2.0 | — | — | — | 2.0 |
| coconut mono-ethanolamide | | — | — | — | 10.0 | — | — |
| cocoamide | | — | — | — | — | 3.0 | — |
| perfume | | 0.5 | 0.5 | 0.5 | 0.5 | 0.5 | 0.5 |
| water | | 26.6 | 57.1 | 42.1 | 33.1 | 40.1 | 47.1 |
| | total | 100.0 | 100.0 | 100.0 | 100.0 | 100.0 | 100.0 |

TABLE III

| | | Percent by weight Example No. | | | | |
|---|---|---|---|---|---|---|
| | | 11 | 12 | 13 | 14 | 15 |
| triethanolamine lauryl sulfate | | 18.4 | — | 18.4 | 18.4 | — |
| sodium lauryl sulfate | | — | 12.8 | — | — | 12.8 |
| polyketone | | 7.5 | 7.5 | 7.0 | 7.0 | 6.5 |
| polyvinyl ethyl ether resin | | 2.5 | 2.5 | — | — | — |
| sucrose acetate isobutyrate | | — | — | 3.0 | 3.0 | 3.5 |
| ethyl alcohol | | 40.0 | 40.0 | 40.0 | 30.0 | 40.0 |
| bis-2-hydroxyethyl cocoamine oxide | | — | 0.6 | — | — | 0.6 |
| cocoamide | | 2.0 | 2.1 | 2.0 | 2.0 | 2.1 |
| perfume | | 0.5 | 0.5 | 0.5 | 0.5 | 0.5 |
| water | | 29.1 | 34.0 | 29.1 | 39.1 | 34.0 |
| | total | 100.0 | 100.0 | 100.0 | 100.0 | 100.0 |

TABLE IV

| | | Percent by weight Example No. | | | | | | |
|---|---|---|---|---|---|---|---|---|
| | | 16 | 17 | 18 | 19 | 20 | 21 | 22 |
| triethanolamine lauryl sulfate | | — | 18.4 | 18.4 | — | — | 18.4 | 18.4 |
| sodium lauryl sulfate | | 11.90 | — | — | 12.40 | 12.8 | — | — |
| hydrogenated rosin | | — | — | — | — | — | — | 5.0 |
| polyketone | | 6.05 | 6.5 | 6.5 | 7.80 | 6.5 | 6.5 | — |
| sucrose acetate isobutyrate | | 1.85 | 3.5 | 3.5 | 3.40 | 3.5 | 3.5 | 2.5 |
| polyvinylacetate | | — | — | — | — | — | — | 2.5 |
| ethyl alcohol | | 40.0 | 40.0 | 40.0 | 40.0 | 40.0 | 40.0 | 40.0 |
| isopropylmyristate | | — | — | — | — | 2.0 | — | — |
| polyethylene glycol 6000 distearate (lubricant) | | — | — | 1.0 | — | — | — | — |
| beeswax | | — | 1.0 | — | — | — | — | — |
| hydroxy-propyl cellulose | | — | — | — | — | — | 0.5 | 0.2 |
| mineral oil | | 7.00 | — | — | 3.00 | — | — | — |
| cocoamide | | 1.95 | 2.0 | 2.0 | 1.95 | 2.1 | 2.0 | 2.00 |
| bis-2-hydroxyethyl cocoamine oxide | | 0.55 | — | — | 5.82 | 0.6 | — | — |
| perfume | | 0.45 | 0.5 | 0.5 | 0.48 | 0.5 | 0.5 | 0.5 |
| water | | 30.25 | 28.1 | 28.1 | 25.14 | 32.0 | 28.6 | 28.85 |
| | total | 100.00 | 100.0 | 100.0 | 100.0 | 100.0 | 100.0 | 100.0 |

TABLE V

| | Percent by weight Example No. | |
|---|---|---|
| | 23 | 24 |
| triethanolamine lauryl sulfate | 18.4 | 18.4 |
| hydrogenated rosin | 5.0 | 20.0 |
| ethyl alcohol | 40.0 | 40.0 |
| perfume | 0.5 | 0.5 |
| water | 36.1 | 36.1 |
| total | 100.0 | 100.0 |

TABLE VI

| | Percent by weight Example No.25 |
|---|---|
| Sodium lauryl sulfate (30.00 active) | 42.60 |
| polyketone | 8.00 |
| sucrose acetate isobutyrate | 2.00 |
| cocoamide | 2.03 |
| bis 2 hydroxyethyl cocoamine oxide (40% active) | 1.68 |
| nydroxypropyl cellulose | 1.00 |
| ethyl alcohol | 41.50 |
| perfume | 0.50 |
| color | 0.15 |
| water | 0.54 |
| | 100.00 |

TABLE VII

| | Percent by weight Example No.26 |
|---|---|
| sodium lauryl sulfate | 42.60 |
| polyketone | 15.00 |
| sucrose acetate isobutyrate | 5.00 |
| cocoamide | 2.03 |
| bis 2 hydroxyethyl cocoamine oxide (40% active) | 1.68 |
| hydroxypropyl cellulose | 1.00 |
| ethyl alcohol | 32.04 |
| perfume | 0.50 |
| color | 0.15 |
| | 100.00 |

TABLE VIII

| | Percent by weight Example No.27 |
|---|---|
| triethanolamine lauryl sulfate | 18.4 |
| monoethyl ether of ethylene glycol | 50.0 |
| polymerized rosin | 10.0 |
| perfume | 0.5 |
| water | 21.1 |
| | 100.0 |

TABLE IX

| | Percent by weight Example No.28 |
|---|---|
| triethanolamine lauryl sulfate | 18.4 |
| isopropyl alcohol | 50.0 |
| hydrogenated rosin | 10.0 |
| perfume | 0.5 |
| water | 21.1 |
| | 100.0 |

TABLE X

| | Percent by weight Example No.29 |
|---|---|
| triethanolamine lauryl sulfate | 20.0 |
| dimethyl ketone | 40.0 |

TABLE X-continued

| | Percent by weight Example No.29 |
|---|---|
| polymerized rosin | 10.0 |
| water | 30.0 |
| | 100.0 |

TABLE XI

| | Percent by weight Example No.30 |
|---|---|
| triethanolamine lauryl sulfate | 20.0 |
| sucrose acetate isobutyrate | 10.0 |
| ethyl alcohol | 40.0 |
| water | 30.0 |
| | 100.0 |

TABLE XII

| | Percent by weight Example No.31 |
|---|---|
| sucrose acetate isobutyrate | 60.0 |
| triethanolamine lauryl sulfate | 20.0 |
| ethyl alcohol | 20.0 |
| | 100.0 |

TABLE XIII

| | Percent by weight Example No.32 |
|---|---|
| polymerized rosin | 60.0 |
| ethyl alcohol | 20.0 |
| triethanolamine lauryl sulfate | 20.0 |
| | 100.0 |

TABLE XIV

| | Percent by weight Example No.33 |
|---|---|
| polymerized rosin | 50.0 |
| ethyl alcohol | 20.0 |
| triethanolamine lauryl sulfate | 20.0 |
| mineral oil | 10.0 |
| | 100.0 |

Each of the above formulations imparted acceptable and beneficial properties to the hair.

As this invention may be embodied in several forms without departing from the spirit or essential character thereof, the present embodiments are illustrative and not restrictive. The scope of the invention is to be defined by the appended claims rather than by the description preceding them and all embodiments which fall within the meaning and range of equivalency of the claims are, therefore, intended to be embraced by those claims.

We claim:

1. A foaming shampoo composition comprising (a) at least about 5 weight percent, based on the weight of the total composition of a surfactant system selected from the group consisting of anionic, nonionic and ampholytic detergent compounds, and mixtures thereof;

b. from about 10 to about 90 weight percent, based on the weight of the total composition of a solvent system, the solvent system containing at least 10 weight percent thereof of a water miscible polar organic solvent; and, c. from about 1.0 to about 60 weight percent based on the weight of the total composition of a hair grooming agent selected from the group consisting of polymerized wood rosin, dimerized wood rosin, hydrogenated wood rosin, $C_1$ to $C_6$ esters of these rosins, sucrose acetate isobutyrate, polyvinyl ethyl ethers having a molecular weight of from about 10,000 to 750,000 alkyds having a molecular weight of from about 10,000 to about 50,000, polyketones having an average molecular weight of from about 500 to 1,000, vinylacetate, acrylic resins having an average molecular weight of from about 10,000 to 150,000, cocoamide having a melting point of 80° to 90°C, steryl amide, ethoxylated higher fatty alcohols, and mixtures thereof, the grooming agent being substantially soluble or dispersible in the solvent-surfactant systems so as to form a single phase with the solvent-surfactant system and substantially insoluble in water so that the agent will become insoluble and deposit onto the hair of the user upon dilution with water during shampooing; the relative amounts of the surfactant system, the solvent system and the hair grooming agent being adjusted within said ranges to give a foaming shampoo composition.

2. A foaming shampoo composition comprising (a) at least about 5 weight percent, based on the weight of the total composition of a surfactant system selected from the group consisting of anionic, nonionic, and ampholytic detergent compounds, and mixtures thereof;

b. from about 10 to about 90 weight percent, based on the weight of the total composition of a solvent system, the solvent system containing at least 10 weight percent thereof of a water miscible polar organic solvent; and, c. from about 1.0 to about 60 weight percent based on the weight of the total composition of a hair grooming agent selected from the group consisting of polymerized wood rosin, dimerized wood rosin, hydrogenated wood rosin, $C_1$ to $C_6$ esters of these rosins, sucrose acetate isobutyrate, polyvinyl ethyl ethers having a molecular weight of from about 10,000 to 750,000, alkyds having a molecular weight of from about 10,000 to 50,000, polyketones having an average molecular weight of from about 500 to 1,000, vinylacetate, acrylic resins having an average molecular weight of from about 10,000 to 150,000 and minutes thereof, the grooming agent being substantially soluble or dispersible in the solvent-surfactant system so as to form a single phase with the solvent-surfactant system and substantially insoluble in water so that the agent will become insoluble and deposit onto the hair of the user upon dilution with water during shampooing; the relative amounts of the surfactant system, the solvent system and the hair grooming agent being adjusted within said ranges to give a foaming shampoo composition.

3. A shampoo composition as defined in claim 2 wherein the composition contains from about 5 to about 60 weight percent based on the total weight of the composition of the surfactant system.

4. A foaming shampoo composition comprising (a) at least about 5 weight percent, based on the weight of the total composition of a surfactant system selected from the group consisting of anionic, nonionic, and ampholytic detergent compounds, and mixtures thereof;

b. from about 10 to about 90 weight percent, based on the weight of the total composition of a solvent system, the solvent system containing at least 10 weight percent thereof of a water miscible polar organic solvent; and, c. from about 1.0 to about 60 weight percent based on the weight of the total composition of a hair grooming agent selected from the group consisting of cocoamide having a melting point of 80 to 90°C, steryl amide, ethoxylated higher fatty alcohols, and mixtures thereof, the grooming agent being substantially soluble or dispersible in the solvent-surfactant systems so as to form a single phase with the solvent-surfactant system and substantially insoluble in water so that the agent will become insoluble and deposit onto the hair of the user upon dilution with water during shampooing; the relative amounts of the surfactant system, the solvent system and the hair grooming agent being adjusted within said ranges to give a foaming shampoo composition.

5. A shampoo composition as defined in claim 4 wherein the composition further contains from about 1 to about 25 weight percent based on the weight of the total composition of a lubricant for hair.

6. A shampoo composition as defined in claim 5 wherein the lubricant is soluble or dispersed in the solvent-surfactant systems and is present from about 1 to about 15 weight percent.

7. A shampoo composition as defined in claim 5 wherein the lubricant is insoluble in the solvent-surfactant systems and is present from about 5 to about 25 weight percent.

8. A shampoo composition as defined in claim 5 wherein the lubricant is selected from the group consisting of isopropyl myristate, isopropyl adipate, glycol polysiloxane, mineral oil and mixtures thereof.

9. A shampoo composition as defined in claim 5 wherein the lubricant is present from about 5 to about 20 weight percent and is selected from the group consisting of vegetable oils, mineral oils, animal oils, lanolin compounds and mixtures thereof.

10. A shampoo composition as defined in claim 4 wherein the composition contains at least about 4 weight percent, based on the weight of the total composition of the hair groom agent.

11. A shampoo composition as defined in claim 4 wherein the solvent system further contains up to about 40 weight percent, based on the weight of the polar organic solvent of a non-polar solvent.

12. A shampoo composition as defined in claim 4 wherein the polar solvent is selected from the group consisting of monohydric alcohols, dihydric alcohols, triols, polyethylene glycols having a molecular weight less than about 400, higher fatty alcohols and mixtures thereof.

13. A shampoo composition as defined in claim 12 wherein said grooming agent is comprised of a mixture of sucrose acetate isobutyrate and polyketone at a ratio of from about 9:1 to 1:9.

14. A shampoo composition as defined in claim 12 wherein said grooming agent is comprised of mixtures of polyketone with at least one component selected from the group consisting of dimerized wood rosin, hydrogenated wood rosin, polymerized wood rosin and mixtures thereof, the ratio of polyketone to said other component being about 1:9 to 9:1.

15. A shampoo composition as defined in claim 12 wherein said composition further contains from about 5 to about 20 weight percent of at least one water imiscible lubricant for hair selected from the group consisting of light mineral oils, fixed oils, lanolin compounds and mixtures thereof.

16. A shampoo composition as defined in claim 12 wherein said composition further contains from about 9 to about 28 weight percent of at least one emulsion destabilizer selected from the group consisting of monohydric alcohols having from 1 to 7 carbon atoms, dihydric alcohols having from 2 to 7 carbon atoms, monoalkyl ethers of aliphatic dihydric alcohols having from 3 to 6 carbon atoms, dialkyl ketones having from 3 to 5 carbon atoms and mixtures thereof.

17. A shampoo composition as defined in claim 12 wherein said composition further contains from about 1 to about 15 weight percent of at least one material selected from the group consisting of isopropyl myristate, isopropyl adipate, glycol polysiloxanes and mixtures thereof.

18. A shampoo composition as defined in claim 12 further comprising from about 0.1 to about 10 weight percent of a hydrophilic thickener.

* * * * *